(12) United States Patent
Nakamura et al.

(10) Patent No.: US 9,810,371 B2
(45) Date of Patent: Nov. 7, 2017

(54) ARM SUPPORT APPARATUS

(71) Applicants: DENSO CORPORATION, Kariya, Aici-pref. (JP); SHINSHU UNIVERSITY, Matsumoto, Nagano (JP); TOKYO WOMEN'S MEDICAL UNIVERSITY, Tokyo (JP)

(72) Inventors: Satoru Nakamura, Kariya (JP); Kazuhiro Hongo, Matsumoto (JP); Tetsuya Goto, Matsumoto (JP); Yosuke Hara, Matsumoto (JP); Jun Okamoto, Tokyo (JP)

(73) Assignees: DENSO CORPORATION, Kariya (JP); SHINSHU UNIVERSITY, Nagano (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 82 days.

(21) Appl. No.: 14/645,156

(22) Filed: Mar. 11, 2015

(65) Prior Publication Data
US 2015/0257843 A1 Sep. 17, 2015

(30) Foreign Application Priority Data
Mar. 12, 2014 (JP) .................................. 2014-048913

(51) Int. Cl.
*A47C 7/54* (2006.01)
*F16M 13/02* (2006.01)
(Continued)

(52) U.S. Cl.
CPC ........... *F16M 13/022* (2013.01); *A47C 7/506* (2013.01); *A47C 7/54* (2013.01); *A61B 90/60* (2016.02);
(Continued)

(58) Field of Classification Search
CPC ........... A47C 7/54; A47C 7/543; A47C 9/027; A47C 9/005; A47C 7/503; A47C 7/50;
(Continued)

(56) References Cited

U.S. PATENT DOCUMENTS 2,614,558 A * 10/1952 Lovell ...................... A61F 5/04
248/118
4,913,393 A * 4/1990 Wood ....................... A61G 5/10
224/407
(Continued)

FOREIGN PATENT DOCUMENTS

JP H10272163 A 10/1998
JP 2009291363 A 12/2009

OTHER PUBLICATIONS

Nikkan Kogyo Shinbun, Ltd., Mechanical Design, Nov. 2013, vol. 57, p. 95.

*Primary Examiner* — Nkeisha Smith
(74) *Attorney, Agent, or Firm* — Oliff PLC

(57) ABSTRACT

In an arm support apparatus, an weight attachment is provided for at least one specified link in links of a support member supporting a mount to be movable based on rotation of at least one of the links around a corresponding at least one of the joints. The at least one specified link is associated with at least one specified degree of freedom. The weight attachment is configured such that one or more weight members are attachable thereto. When the one or more weight members are attached to the weight attachment, the weight attachment is configured to substantially balance in weight with the mount on which the part of the arm is mounted while applying supporting force to the part of the arm mounted on the mount.

4 Claims, 7 Drawing Sheets

(51) Int. Cl.
*A47C 7/50* (2006.01)
*A61B 90/60* (2016.01)
*A61B 90/50* (2016.01)

(52) U.S. Cl.
CPC ... *A61B 2090/504* (2016.02); *A61B 2090/508* (2016.02)

(58) Field of Classification Search
CPC .......... A47C 7/506; A47C 7/52; A47C 7/546; F16M 13/022; A61B 90/60; A61B 2090/504; A61B 2090/508; A61G 2203/10
USPC ............ 248/276.1, 228.51, 118; 297/411.38, 297/411.33, 173
See application file for complete search history.

(56) References Cited

U.S. PATENT DOCUMENTS

| | | | | |
|---|---|---|---|---|
| 5,281,001 A * | 1/1994 | Bergsten | ............ | A47B 21/0371 248/118 |
| 5,571,274 A * | 11/1996 | Holstensson | ............ | A47C 1/03 248/118.3 |
| 5,927,815 A * | 7/1999 | Nakamura | ............ | F16C 11/106 248/276.1 |
| 6,619,747 B2 * | 9/2003 | Ko | ............ | A47C 7/54 248/118.3 |
| 6,773,071 B1 * | 8/2004 | Stasney | ................. | A47C 7/546 248/118.3 |
| 6,923,505 B2 * | 8/2005 | Siminovitch | ............ | A47C 7/54 248/118.1 |
| 7,600,819 B2 * | 10/2009 | Armo | .................. | B60N 2/4633 297/411.3 |
| 7,823,843 B2 * | 11/2010 | Oberlaender | ........ | F16M 11/046 248/118 |
| 8,113,590 B2 * | 2/2012 | Stuijt | ...................... | A61G 5/12 297/411.35 |
| 8,480,168 B2 * | 7/2013 | Turner | .................. | A61B 90/60 297/195.11 |
| 9,486,289 B2 * | 11/2016 | Okuda | .................. | A61B 90/60 |
| 2006/0202541 A1 * | 9/2006 | Armo | .................. | B60N 2/4633 297/411.35 |
| 2014/0014804 A1 * | 1/2014 | Okuda | .................. | F16M 13/04 248/550 |
| 2015/0202017 A1 * | 7/2015 | Nakamura | ............ | A61G 15/10 248/118 |

* cited by examiner

ARM SUPPORT APPARATUS

CROSS REFERENCE TO RELATED APPLICATIONS

This application is based on and claims the benefit of priority from Japanese Patent Application 2014-048913 filed on Mar. 12, 2014, the disclosure of which is incorporated in its entirety herein by reference.

TECHNICAL FIELD

The present disclosure relates to arm support apparatuses that support an arm of an operator.

BACKGROUND

For precise and/or long manual operations, such as neurosurgical operations, there are known arm support apparatuses for supporting an arm of an operator such as a doctor who performs surgical operations. An example of these arm support apparatuses is disclosed in Japanese Patent Application Publication No. H10-272163, referred to as a first patent publication. An arm support apparatus disclosed in the first patent publication is equipped with a movable multijoint arm having a mount portion at an end thereof. The forearm of an operator's arm is fixedly mounted on the mount portion with a belt, which allows the mount portion to follow motion of the supported arm. The arm support apparatus locks the movable multijoint arm when a foot switch is operated by the operator, thus preventing motion of the mount portion.

The arm support apparatus disclosed in the first patent publication necessitates unfastening and fastening the belt each time the operator's arm is dismounted from the mount portion for placing instrument, such as tweezers, on a table. This may result in the operator's usability of the arm support apparatus deteriorating.

In order to address such a problem, there is known an arm support apparatus, which is disclosed in Japanese Patent Application Publication No. 2009-291363, referred to as a second patent publication.

The arm support apparatus disclosed in the second patent publication urges the mount portion upward from the lower side of the mount portion with springs to bring the mount portion into contact with the forearm of an operator's arm based on friction force between the forearm and the mount portion. This permits the operator to easily mount a forearm on the mount portion or dismount a forearm from the mount portion.

SUMMARY

While the operator moves the forearm mounted on the mount portion to cause the mount portion to follow movement of the forearm, the forearm is constantly urged upward from the mount portion. As described above, the springs apply the urging force to the forearm. That is, the urging force based on the springs constantly urge the mount portion toward a predetermined standby position, and serves as supporting force to be applied to the forearm.

The urging force generated by the springs, which serves as the supporting force to be applied to the forearm, changes depending on the location of the mount portion. This may provide a feeling of strangeness to the operator, resulting in need of improvements for the arm support apparatus disclosed in the second patent publication.

In addition, it may be difficult for the arm support apparatus disclosed in the second patent publication to adjust the supporting force to be applied to the forearm to a desired level.

One aspect of the present disclosure therefore seeks to provide arm support apparatuses; the arm support apparatuses are capable of addressing the circumstances set forth above.

Specifically, an alternative aspect of the present disclosure aims to provide such arm support apparatuses, each of which is capable of maintaining supporting force at a desired value independently of the position of a mount on which a part of an operator's arm is mounted.

According to an exemplary aspect of the present disclosure, there is provided an arm support apparatus to be installed on a reference plane for supporting an arm of an operator. The arm support apparatus includes a mount on which a part of the arm of the operator is mountable. The arm support apparatus includes a support member including a plurality of links and a plurality of joints each rotatably supporting at least one of the plurality of links. The support member supports the mount to be movable based on rotation of at least one of the plurality of links around a corresponding at least one of the plurality of joints. The plurality of joints provide several degrees of freedom. The several degrees of freedom include at least one specified degree of freedom around an axis of at least one joint in the plurality of joints. The axis of the at least one joint is directed to cross a vertical direction of the reference plane. The arm support apparatus includes a weight attachment provided for at least one specified link in the plurality of links. The at least one specified link is associated with the at least one specified degree of freedom. The weight attachment is configured such that one or more weight members are attachable thereto. When the one or more weight members are attached to the weight attachment, the weight attachment is configured to balance in weight with the mount on which the part of the arm is mounted while applying supporting force to the part of the arm mounted on the mount.

With the arm support apparatus according to the exemplary aspect, the weight attachment is configured such that the one or more weight members are attachable thereto. The weight attachment, to which the one or more weight members are attached, balances in weight with the mount on which the part of the arm is mounted while applying supporting force to the part of the arm mounted on the mount. Specifically, this configuration applies the supporting force to the part of the operator's arm mounted on the mount based on total weight of the one or more weigh members without using elastic members, such as springs. Thus, the arm support apparatus makes it possible to maintain the supporting force applied to the part of the operator's arm mounted on the mount at a desired value independently of the position of the mount.

Various aspects of the present disclosure can include and/or exclude different features, and/or advantages where applicable. In addition, various aspects of the present disclosure can combine one or more feature of other embodiments where applicable. The descriptions of features, and/or advantages of particular embodiments should not be construed as limiting other embodiments or the claims.

BRIEF DESCRIPTION OF THE DRAWINGS

Other aspects of the present disclosure will become apparent from the following description of embodiments with reference to the accompanying drawings in which.

DETAILED DESCRIPTION OF EMBODIMENT

Figure 1:
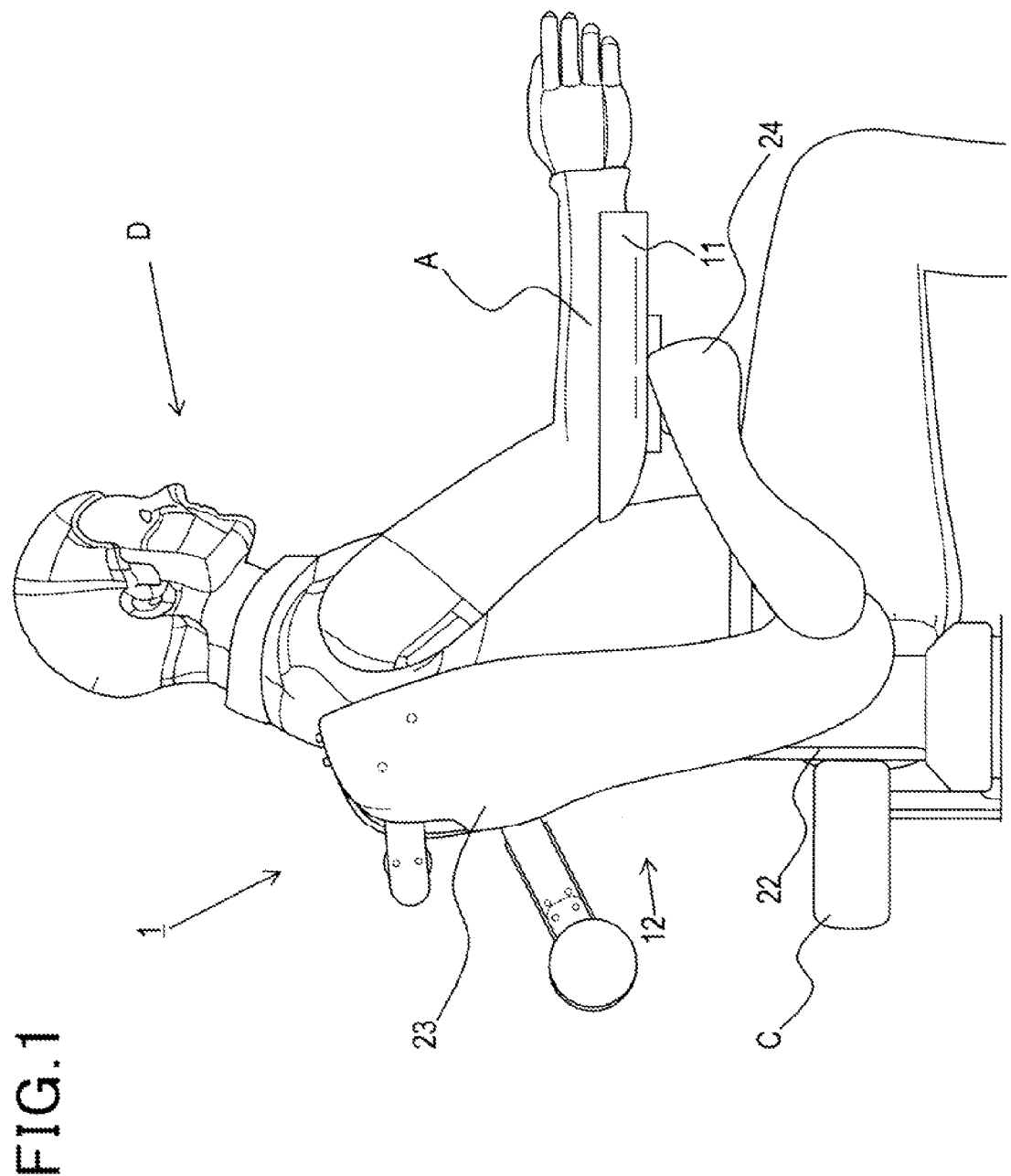
FIG. 1 is a schematic right side view of an arm support apparatus according to an embodiment of the present disclosure.

An embodiment of the present disclosure will be described hereinafter with reference to the accompanying drawings. In the drawings, identical reference characters are utilized to identify identical corresponding components. In the following embodiment, there is described an arm support apparatus for supporting an arm, especially a forearm, of a doctor as an example of operators who performs medical operations, such as surgical operations. However, arm support apparatuses according to the present disclosure can be designed to support an arm of an operator who performs precise and/or long operations during a process of, for example, manufacturing a machine, such as precision machines.

Figure 2:
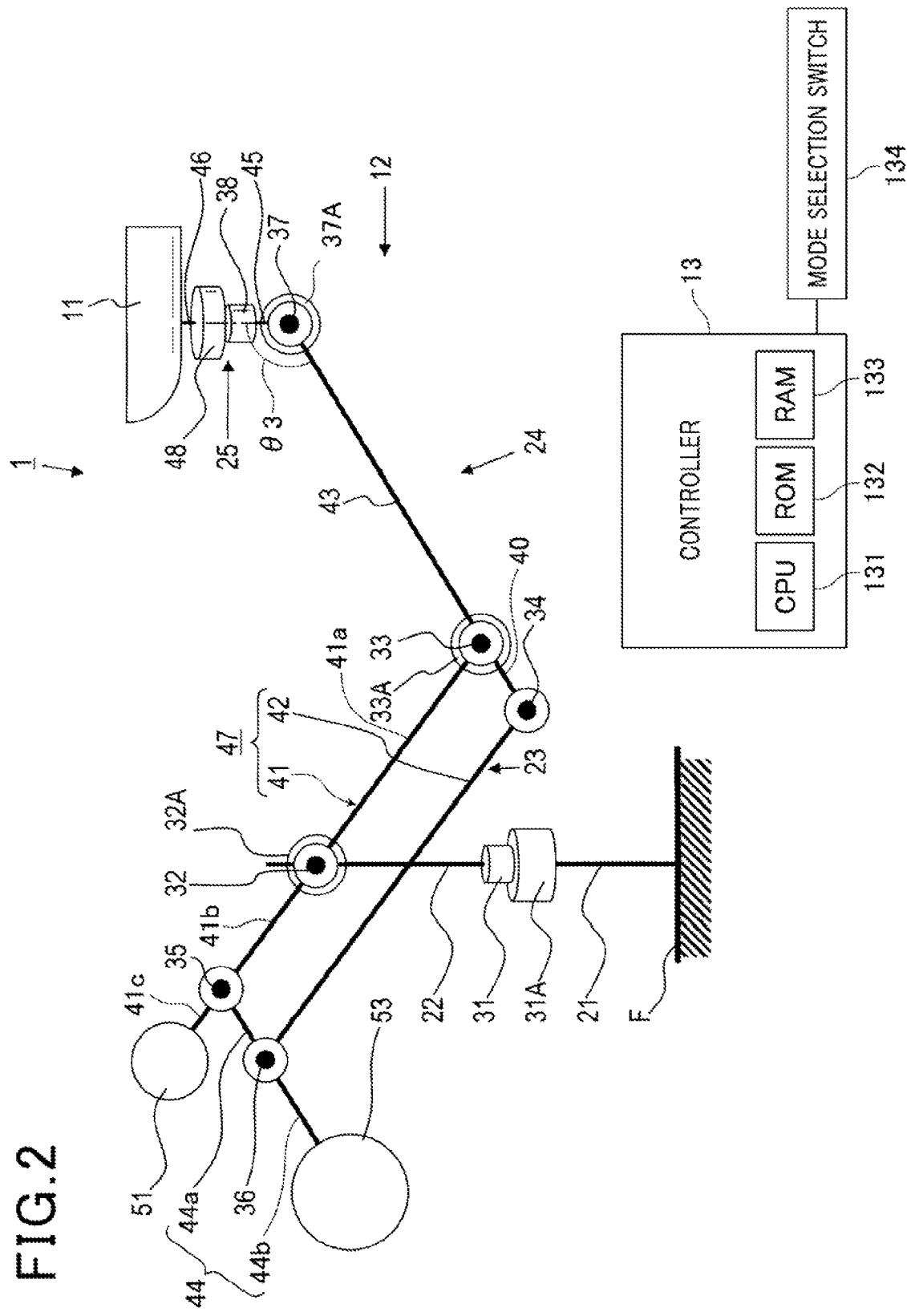
FIG. 2 is a schematic view of a link mechanism of the arm support apparatus illustrated in FIG. 1.

FIG. 1 schematically illustrates a right-side view of an arm support apparatus 1 according to the embodiment of the present disclosure, and FIG. 2 schematically illustrates a link mechanism of the arm support apparatus 1.

Referring to FIGS. 1 and 2, the arm support apparatus 1 is equipped with an arm holder 11, a multijoint arm 12, and a controller 13. Referring to FIG. 1, when a doctor D uses the arm support apparatus 1, the doctor D prepares a chair C and locates the chair C by the arm support apparatus 1. Then, the doctor D sits on the chair C, and puts a forearm A of the dominant arm, e.g. the right arm, on the arm holder 11 while sitting on the chair C.

The arm holder 11 is operative to hold the forearm A of the dominant arm of a doctor D.

The controller 13 is communicably connected to the multijoint arm 11 and is operative to control an operation mode of the arm support apparatus 1.

Referring to FIG. 1, the multijoint arm 12 is designed as a movement mechanism that movably supports the arm holder 11 according to external force applied to the arm holder 11. As schematically illustrated in FIG. 2, the multijoint arm 12 is comprised of, for example, eight joints 31, 32, 33, 34, 35, 36, 37, and 38 that provide five degrees of freedom corresponding to the joints 31, 32, 33, 37, and 38.

The multijoint arm 12 is also comprised of a base 21, a shoulder 22, and six rigid links 40, 41, 42, 43, 44, 45, and 46. Each of the joints 31 to 38 is a rotational joint having an axis and is configured such that two members in the members 21, 22, and 40 to 46 adjacent to the joint are connected to the joint to be rotatable about the axis. Hereinafter, the rigid links 40 to 46 are designed as a linear bar link, but a curved bar link or a linear or curved plate link can be used for each of the rigid links 40 to 46.

The base 21 is located facing upwardly on a floor F of an operating room, which serves as, for example, a reference plane for the arm support apparatus 1, to support the multijoint arm 12. For example, the base 21 is equipped with casters (not shown) located at a bottom portion thereof, so that the base 21 is easily movable on the floor F. The base 21 also has a stopper (not shown) provided for each of the casters. A doctor or an assistant manipulates the stopper for each caster to stop the movement of the caster. This makes it possible to fixedly locate the base 21 at a desired position on the floor F, such as a position by the chair C located on the floor F (see FIG. 1).

The joint 31 has a reference vertical axis perpendicular to, for example, the floor F, and is mounted on a first longitudinal end of a top of the base 21 such that the vertical axis is perpendicular to the floor F.

On the joint 31, a first end of the shoulder 22 is mounted. On a second end of the shoulder 22, the joint 32 having a horizontal axis is mounted. The shoulder 22 is rotatable about the vertical axis of the joint 31.

For example, the first arm member 23 is designed as a parallel link mechanism 47 comprised of the rigid links 41 and 42 equal in length to each other. The rigid links 41 and 42 are capable of moving while keeping the rigid links 41 and 42 parallel to each other with a constant space therebetween.

The rigid link 41 is comprised of a first link member 41a, a second link member 41b, and a third link member 41c. The first link member 41a is longer in length than the second link member 41b. Each of the first and second link members 41a and 41b has a first end joined to the horizontal axis of the joint 32 to be swingable about the horizontal axis of the joint 32. The second end of the first link 41a is joined to the joint 33, which has a horizontal axis parallel to the joint 32, so as to be swingable about the horizontal axis of the joint 33. The second arm member 24 is comprised of the rigid link 43 having a first end and a second end. The first end of the rigid link 43 is joined to the joint 33 to be swingable about the horizontal axis of the joint 33.

The rigid link 42 has a first end and a second end opposite to the first end. The first end of the rigid link 42 is joined to the joint 34 having a horizontal axis parallel to the horizontal axis of the joint 32. The link 40 has both ends swingably joined to the respective joints 33 and 34.

The second end of the second link member 41b is joined to the joint 35, which has a horizontal axis parallel to the horizontal axis of the joint 32, to be swingable about the horizontal axis of the joint 35. The second end of the rigid link 42 is joined to the joint 36, which has a horizontal axis parallel to the horizontal axis of the joint 32, to be swingable about the horizontal axis of the joint 36.

The rigid link 44 is comprised of a first link member 44a and a second link member 44b. The first link member 44a, which is equal in length to the link 40, has both first and second ends swingably joined to the respective joints 35 and 36.

That is, the joints 33, 34, 35, and 36 constitute four corners of a parallelogram shape. The opposite sides, i.e. links 41 and 42, of a first pair are equal in length and parallel to each other, and the opposite sides, i.e. links 40 and 44a, of a second pair are equal in length and parallel to each other. This configuration provides a so-called four-joint link.

The second end of the rigid link 43 is joined to the arm holder 11 via an arm-holder support member 25. The arm-holder support member 25 is comprised of the joint 37, the rigid link 45, the joint 38, and the rigid link 46.

Specifically, the second end of the rigid link 43 is joined to the joint 37, which has a horizontal axis parallel to the horizontal axis of the joint 32, to be swingable about the horizontal axis of the joint 37.

The rigid link 45 has a first end and a second end opposite to the first end. The first end of the rigid link 45 is joined to the joint 37 to be swingable about the horizontal axis of the joint 37. The joint 38 is attached to the rigid link 45 to be rotatable about the rigid link 45. The rigid link 45 is continuously joined to a first end of the rigid link 46, and a second end of the rigid link 46 opposite to the first end thereof is joined to, for example, a substantially center portion of the arm holder 11. The arm holder 11 and the rigid link 46 are rotatable about the axis of the joint 38. A force sensor 48 is attached to the rigid link 46 for measuring force applied to the arm holder 11. The set of the arm holder 11, the rigid link 46, the joint 38, and the rigid link 45 is swingable about the horizontal axis of the joint 37.

From the second end of the second link member 41b, the third link member 41c of the rigid link 41 extends through the joint 35 to be away from the joint 35 by a preset length so as to be swingable about the horizontal axis of the joint 35. To the extending end of the third link member 41c, a counterweight structure 51 is attached.

Similarly, from the second end of the first link member 44a of the rigid link 44, to which the joint 36 is joined, the second link member 44b extends through the joint 36 to be away from the joint 36 by a preset length so as to be swingable about the horizontal axis of the joint 36. To the extending end of the second link member 44b, a counterweight structure 53 is attached.

The detailed structure of each of the counterweight structures 51 and 53 will be described later. In addition, how to adjust each of the counterweight structures 51 and 53 will be described later.

To the joint 31, a brake, such as an electromagnetic brake, 31A is attached for reducing, i.e., limiting, rotation of the shoulder 22 relative to the base 21 around the vertical axis of the joint 31.

Like the joint 31, to the joint 32, a brake, such as an electromagnetic brake, 32A is attached for reducing rotation of each of the first and second link members 41a and 41b relative to the shoulder 22 around the horizontal axis of the joint 32.

Additionally, to the joint 33, a brake, such as an electromagnetic brake, 33A is attached for reducing rotation of the rigid link 43, rotation of the link 44a, and rotation of the 41a relative to the joint 33 around the horizontal axis of the joint 33.

To the joint 37, a brake, such as an electromagnetic brake, 37A is attached for reducing rotation of the rigid link 43 and rotation of the rigid link 45 relative to the joint 37 around the horizontal axis of the joint 37.

Each of the brakes 31A to 33A and 37A is communicably connected to the controller 13, and can be controlled by the controller 13.

The controller 13 is, for example, designed as an electronic control circuit equipped with, for example, a CPU 131, a ROM 132, and a RAM 133.

The CPU 131 is programmed to set an operation mode of the arm support apparatus 1 to, for example, one of a lock mode and a free mode.

The lock mode is designed assuming that a doctor D mounts the forearm A of the dominant arm on the arm holder 11 while the arm holder 11 is locked, i.e., fixed to a desired position.

Specifically, in the lock mode, the CPU 131 activates the brakes 31A, 32A, 33A, and 37A to stop movement of the corresponding joints 31, 32, 33, and 37, respectively. This results in prevention of movement of the arm holder 11. Thus, in the lock mode, the doctor D can freely move the dominant arm to perform fine surgical operations on an affected site using the hand of the dominant arm while movement of the arm holder 11 is locked. That is, even if the doctor D removes the forearm A from the arm holder 11, the arm holder 11 is locked.

In the lock mode, because no brake is provided for the joint 38, the doctor D can easily turn the arm holder 11 around the vertical axis of the joint 38 in order to allow small movements of the dominant arm and fine surgical operations on an affected site.

The free mode is designed assuming that a doctor D tries to make the arm holder 11, on which the forearm A is mounted, follow movement of the dominant arm using friction resistance between the forearm A and the arm holder 11. That is, in the free mode, the CPU 131 deactivates the brakes 31A, 32A, 33A, and 37A to allow movement of the corresponding joints 31, 32, 33, and 37, respectively. This results in free movement of the arm holder 11. In the free mode, the doctor D can easily move the arm holder 11 to follow movement of the dominant arm using weak force applied to the arm holder 11 via the forearm A.

As described above, the CPU 131 is capable of selecting one of the lock mode and the free mode. In the embodiment, there can be various measures to instruct the CPU 131 to select one of the lock mode and the free mode.

As an example of the measures according to the embodiment, the arm support apparatus 1 includes a mode selection switch 134 designed as, for example, a foot switch and communicably connected to the CPU 131. Specifically, the CPU 131 can select one of the lock mode and the free mode according to how a doctor or an assistant depresses the mode selection switch 134.

As another example of the measures according to the embodiment, the arm support apparatus 1 includes a force sensor 48 illustrated in FIG. 2. The force sensor 48 is communicably connected to the controller 13. The force sensor 48 is operative to measure force applied to the arm holder 11, at least one of first force, second force, and third force respectively applied to the arm holder 11 via the forearm A. The force sensor 48 is operative to output data, i.e., force data, indicative of the measured force to the controller 13. The CPU 131 is programmed to select one of the lock mode and the free mode according to, for example, magnitude of the measured force represented by the force data.

Next, an example of the detailed structure of each of the counterweight structures 51 and 53 will be described hereinafter with reference to FIG. 3.

Figure 3:
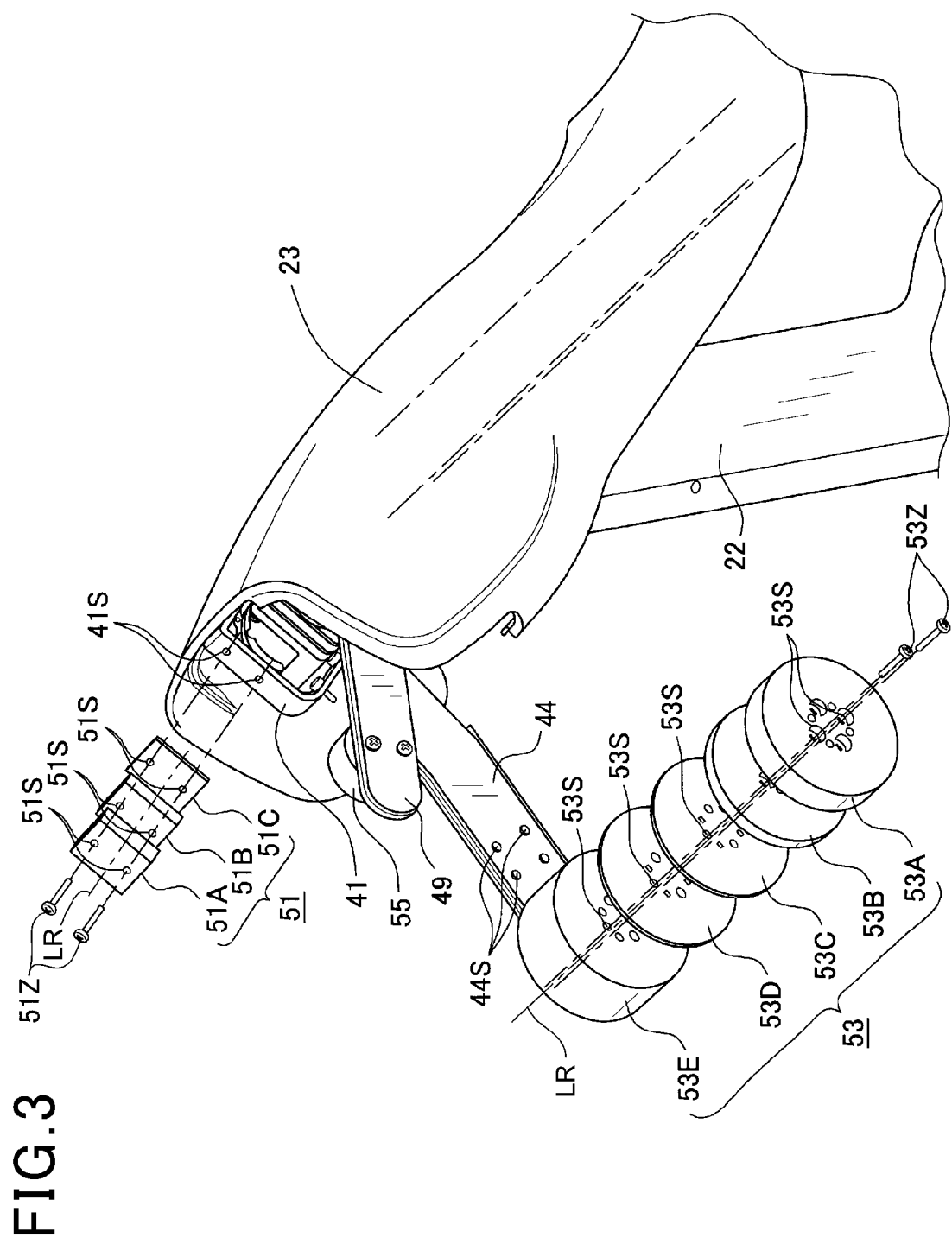
FIG. 3 is an enlarged perspective view schematically illustrating an example of each of counterweight structures of the arm support apparatus illustrated in FIG. 1.

Referring to FIG. 3, the counterweight structure 51 is designed as a combination of a plurality of weight members 51A, 51B, and 51C respectively having, for example, weights different from each other and having a reference line LR passing through predetermined points thereof. FIG. 3 illustrates only three weight members 51A, 51B, and 51C, but the counterweight structure 51 can be designed as a combination of given weights.

Specifically, the extending end of the third link member 41c of the rigid link 41 is formed with a pair of threaded holes 41S to which a pair of screws 51Z is threadable. The threaded holes 41S are placed in a line with a predetermined pitch.

For example, each of the weight members 51A, 51B, 51C has a rectangular parallelepiped plate-like shape. Each of the weight members 51A, 51B, and 51c has a pair of through holes 51S arranged in a line with the same pitch as the pitch of the threaded holes 41S. The through holes 51S of the respective weight members 51A to 51C can be aligned with each other when the weight members 51A to 51C are stacked on each other, and the screws 51Z can pass through the respective through holes 51S of each of the weight members 51A, 51B, and 51C.

With this counterweight structure 51, a desired number of weight member(s) in the weight members 51A to 51C are mounted on the extending end of the third link member 41c of the rigid link 41 while the threaded holes 41S are aligned with the through holes 51S of the desired number of weight member(s). Then, the screws 51Z are inserted through the through holes 51S of the desired number of weight member(s) to be threaded into the respective threaded holes 41S, so that the desired number of weight member(s) in the weight members 51A to 51C are fixedly attached to the extending end of the third link member 41c. This counterweight structure 51 makes it possible for a doctor D or an assistant to easily adjust the weight of the counterweight structure 51 to a desired weight. The threaded holes 41S and the screws 51Z serve as, for example, a weight attachment.

Referring to FIG. 3, the counterweight structure 53 is designed as a combination of a plurality of weight members 53A, 53B, 53C, 53D, and 53E respectively having, for example, weights different from each other and having a reference line LR passing through predetermined points thereof. FIG. 3 illustrates only five weight members 53A to 53E, but the counterweight structure 53 can be designed as a combination of given weights.

Specifically, the extending end of the second link member 44b of the rigid link 44, which is swingable by the joint 36, is formed with plural pairs of threaded holes 44S for fixing at least one of the weight members 53A to 53E to the extending end of the second link member 44b. To each pair of threaded holes 44S, a pair of screws 53Z is threadable. The threaded holes 44S of each pair are placed in a line parallel to a lateral direction of the second link member 44b perpendicular to the length direction of the second link member 44b. The plural pairs of threaded holes 44S are arranged in the length direction of the second link member 44b with predetermined pitches therebetween.

For example, each of the weight members 53A to 53E has a circular plate-like shape. Each of the weight members 53A to 53E has a pair of through holes 53S arranged in a line with the same pitch as the pitch of the threaded holes 44S of each pair. The through holes 53S of the respective weight members 53A to 53E can be aligned with each other when the weight members 53A to 53E are stacked on each other, and the screws 53Z can pass through the respective through holes 53S of each of the weight members 53A to 53E.

With this counterweight structure 53, a desired number of weight member(s) in the weight members 53A to 53E are mounted on the extending end of the second link member 44b while the threaded holes 44S of a selected pair are aligned with the through holes 53S of the desired number of weight member(s). Then, the screws 53Z are inserted through the through holes 53S of the desired number of weight member(s) to be threaded into the respective threaded holes 44S of the selected pair. As a result, the desired number of weight member(s) in the weight members 53A to 53E are fixedly attached to the extending end of the second link member 44b. The threaded holes 44S and the screws 53Z serve as, for example, a weight attachment.

Thus, this counterweight structure 53 makes it possible for a doctor D or an assistant to easily adjust the weight of the counterweight structure 53 to a desired weight. In addition, selection of any pair of threaded holes 44S in the plural pairs of threaded holes 44S, through which the screws 53Z are inserted while the desired number of weight member(s) in the weight members 53A to 53E are mounted, makes it possible to adjust the minimum distance of the center axis of the counterweight structure 53 relative to the joint 36. The center axis of the counterweight structure 53 represents a line passing through the centers, i.e., predetermined points, of the respective weight members 53A to 53E Although omitted in illustration in FIG. 2, a rigid link 49 is attached to the second end of the first link member 44a (see FIG. 4). Swing of the rigid link 45 about the horizontal axis of the joint 37 is transferred to the rigid link 49 via the parallel link mechanism 47.

The rigid link 49 extends to be away from the joint 36 in a direction between the extending direction of the third link member 41c of the rigid link 41 and the extending direction of the second link member 44b of the rigid link 44. To the extending end of the rigid link 49, a counterweight structure 55 is attached.

Figure 4:
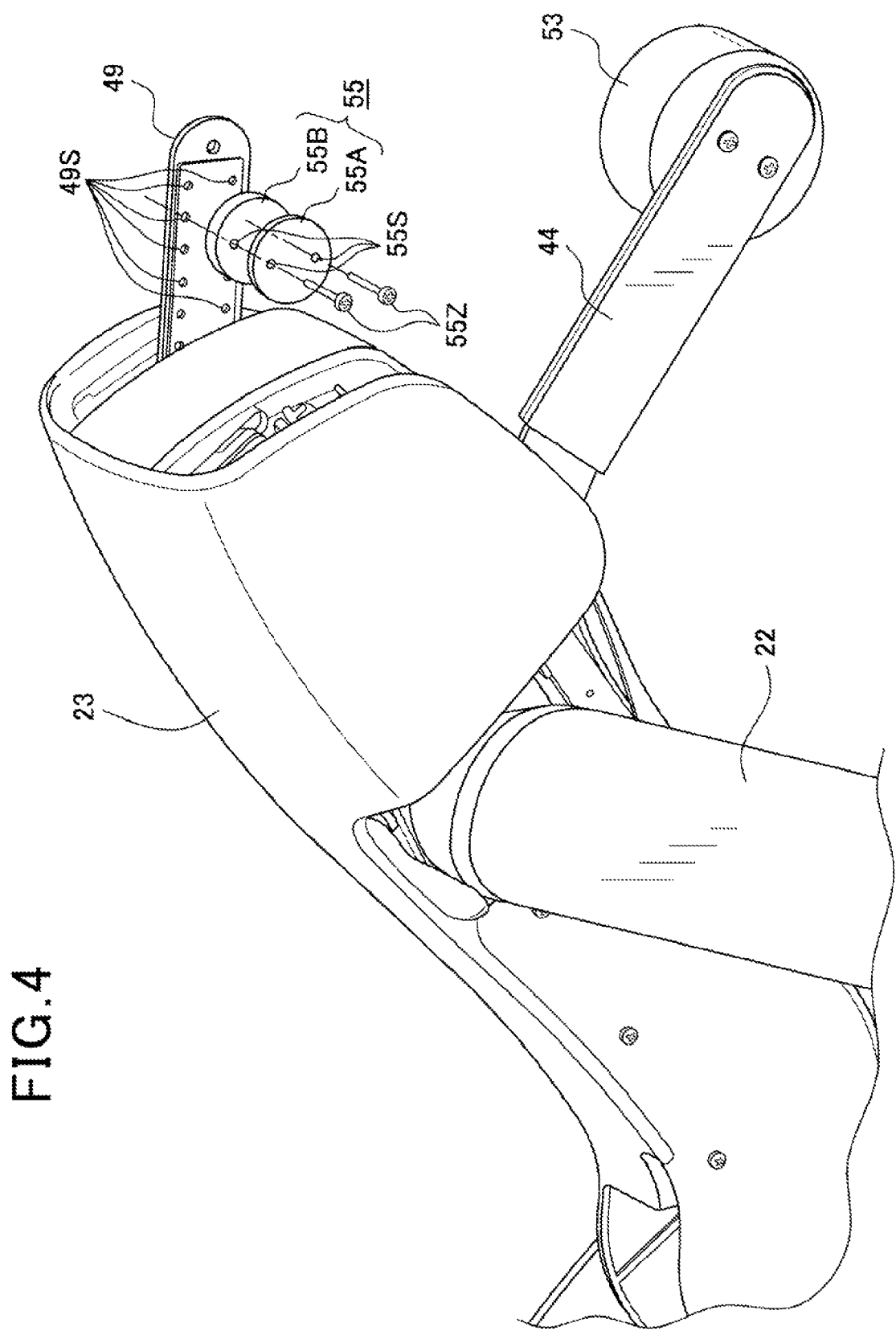
FIG. 4 is an enlarged perspective view schematically illustrating an example of another counterweight structures of the arm support apparatus illustrated in FIG. 1.

Referring to FIG. 4, the counterweight structure 55 is designed as a combination of a plurality of weight members 55A and 55B respectively having, for example, weights different from each other. FIG. 4 illustrates only two weight members 55A and 55B, but the counterweight structure 55 can be designed as a combination of given weights.

Specifically, the extending end of the rigid link 49, which is swingable by the joint 36, is formed with plural pairs of threaded holes 49S for fixing at least one of the weight members 55A and 55B to the extending end of the rigid link 49. To each pair of threaded holes 49S, a pair of screws 55Z is threadable. The threaded holes 49S of each pair are placed in a line parallel to a lateral direction of the rigid link 49 perpendicular to the length direction of the rigid link 49. The plural pairs of threaded holes 49S are arranged in the length direction of the rigid link 49 with predetermined pitches therebetween.

For example, each of the weight members 55A and 55B has a circular plate-like shape. Each of the weight members 55A and 55B has a pair of through holes 55S arranged in a line with the same pitch as the pitch of the threaded holes 49S of each pair. The through holes 55S of the respective weight members 55A and 55B can be aligned with each other when the weight members 55A and 55B are stacked on each other, and the screws 55Z can pass through the respective through holes 55S of each of the weight members 55A and 55B.

With this counterweight structure 55, a desired number of weight member(s) in the weight members 55A and 55B are mounted on the extending end of the rigid link 49 while the threaded holes 49S of a selected one pair are aligned with the through holes 55S of the desired number of weight member(s). Then, the screws 55Z are inserted through the through holes 55S of the desired number of weight member(s) to be threaded into the respective threaded holes 49S of a selected one pair. As a result, the desired number of weight member(s) in the weight members 55A and 55B are fixedly attached to the extending end of the rigid link 49. The threaded holes 49S and the screws 55Z serve as, for example, a weight attachment.

Thus, this counterweight structure 55 makes it possible for a doctor D or an assistant to easily adjust the weight of the counterweight structure 55 to a desired weight. In addition, selection of any pair of threaded holes 49S in the plural pairs of threaded holes 49S, through which the screws 55Z are inserted while the desired number of weight member(s) in the weight members 55A and 55B are mounted, makes it possible to adjust the minimum distance of the center axis of the counterweight structure 55 relative to the joint 36. The center axis of the counterweight structure 55 represents a line passing through the centers, i.e., predetermined points, of the respective weight members 55A and 55B.

The counterweight structures 51, 53, and 55 serve as, for example, a biasing mechanism, and are operative to, when the forearm A of a doctor D is mounted on the arm holder 11, apply counterbalance force to the arm holder 11.

The biasing force applied to the arm holder 11 counterbalances the sum of the weight of the arm holder 11 and the weight of the forearm A held by the arm holder 11. The sum of these weights will be referred to as an arm total weight hereinafter.

This balance supports the forearm A mounted on the arm holder 11.

Note that the biasing force should be ideally counterbalanced to the arm total weight.

However, the hand of the forearm A of a doctor D normally performs surgical operations on an affected site of a living body, such as a patient, from above. Thus, in consideration of this matter, the biasing force, referred to as supporting force, is determined to bias, with very weak force, the arm holder 11 in the upward direction. Note that the upward direction means a direction relative to the affected site which is receiving surgical treatment from the hand of a doctor D, and thereby treatment of the affected site can be safely performed while the arm holder 11 is prevented from being unintentionally lowered.

Next, how to adjust the weight of each of the counterweight structures 51 and 53 will be described hereinafter. Hereinafter, in order to simply describe how to adjust the weight of each of the counterweight structures 51 and 53, it is assumed that an influence of the counterweight structure 55 and the rigid link 49, and an influence of swinging of the arm holder 11 about the horizontal axis of the joint 37 can be ignored.

Figure 5:
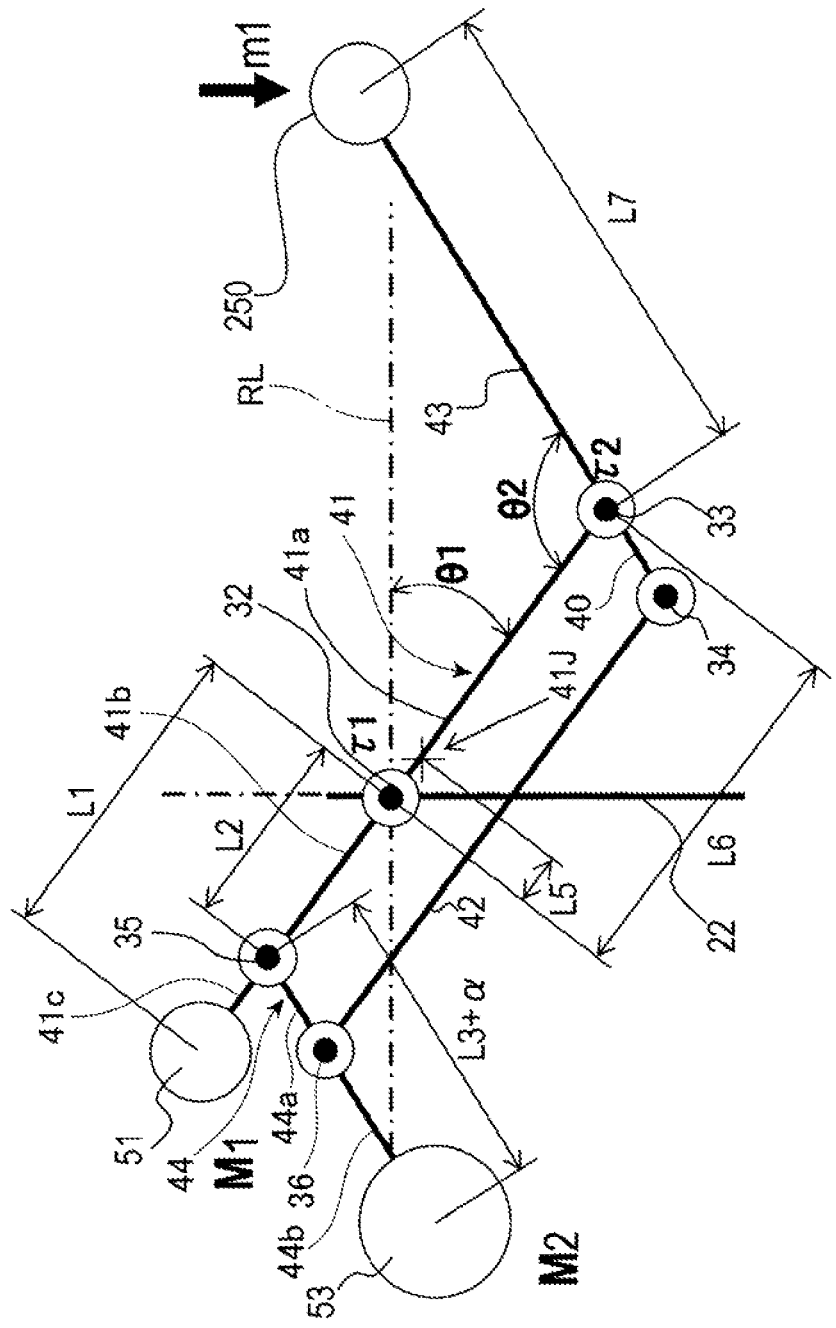
FIG. 5 is a schematic view of a part of the link mechanism illustrated in FIG. 2, which is used to describe how to adjust each of the counterweight structures illustrated in FIG. 3.

Under this assumption, as illustrated in FIG. 5, it can be assumed that a weight 250 based on the weight of the forearm A, which is precisely determined in consideration of desired supporting force for supporting the forearm A upward, and the weight of the arm holder 11 is attached to the joint 37. Because swinging of a portion of the multijoint arm 12 about a given vertical axis does not have an impact on the supporting force, the joints 31 and 38 can be ignored. Thus, a system comprised of the joints 32 to 36 having a first degree of freedom about the horizontal axis of the joint 32 and a second degree of freedom about the horizontal axis of the joint 33 should be considered.

Referring to FIG. 5, a value of the weight 250, a value of the counterweight 51, and a value of the counterweight 53 will be respectively referred to as m1, M1, and M2. The height of the joint 32 relative to the floor F is maintained constant independently of movement of the arm holder 11. Thus, let us consider the potential energies of respective parts (rigid links, counterweight structures, and the weight 250) of the multijoint arm 12.

An angle formed by the rigid link 41 and a line RL extending horizontally from the joint 32 perpendicular to the horizontal axis of the joint 32 is referred to as is referred to as $\theta 1$. A minimum distance between the center axis of the counterweight structure 51 and the horizontal axis of the joint 32 is referred to as a distance L1. At that time, the potential energy PE(51) of the counterweight structure 51 is given as the following equation:

$$PE(51) = M1g \cdot L1 \cdot \sin \theta 1$$

Where g represents acceleration of gravity.

An angle formed by the rigid link 41 and the rigid link 43 is referred to as $\theta 2$. A minimum distance between the horizontal axis of the joint 32 and the horizontal axis of the joint 35 is referred to as a distance L2, and a minimum distance between the center axis of the counterweight structure 53 and the horizontal axis of the joint 35 is referred to as a distance $(L3+\alpha)$. At that time, the potential energy PE(53) of the counterweight structure 53 is given as the following equation:

$$PE(53) = M2g \cdot \{L2 \cdot \sin \theta 1 - (L3+\alpha) \cdot \sin(\pi - \theta 1 - \theta 2)\}$$

Note that the reason why the minimum distance between the center axis of the counterweight structure 53 and the horizontal axis of the joint 35 is referred to as the distance $(L3+\alpha)$ is that the minimum distance changes depending on which pair of the threaded holes 44 is selected.

When a minimum distance between a center 41J of the rigid link 41 and the horizontal axis of the joint 32 is referred to as L5, and a weight of the rigid link 41 is referred to as M41, the potential energy PE(41) of the rigid link 41 is given as the following equation:

$$PE(41) = -M41g \cdot L5 \cdot \sin \theta 1$$

A minimum distance between the horizontal axis of the joint 32 and the horizontal axis of the joint 33 is referred to as L6, and a minimum distance between the horizontal axis of the joint 32 and the center of the weight 250 is refereed to as L7. At that time, the potential energy PE (250) of the weight 250 is given as the following equation:

$$PE(250) = M1g \cdot \{-L6 \cdot \sin \theta 1 + L7 \cdot \sin(\pi - \theta 1 - \theta 2)\}$$

After calculation of the potential energies of respective parts (rigid links, counterweight structures, and the weight 250) of the multijoint arm 12 set forth above, the sum U of the potential energies PE(51), PE(53), PE(41), . . . , PE(250) is calculated. Thereafter, the sum U of the potential energies PE(51), PE(53), PE(41), . . . , PE(250) is differentiated with respect to $\theta 1$, so that torque $\tau 1$ about the horizontal axis of the joint 32 is obtained. In addition, the sum U of the potential energies PE(51), PE(53), PE(41), . . . , PE(250) is differentiated with respect to $\theta 2$, so that torque $\tau 2$ about the horizontal axis of the joint 33 is obtained.

Regarding the torque $\tau 1$ around the horizontal axis of the joint 32 and the torque $\tau 2$ about the horizontal axis of the joint 33, the following equations (1) and (2) are established:

$$\tau 1 = A \cos \theta 1 + \tau 2 \quad (1)$$

$$\tau 2 = B \cos(\theta 1 + \theta 2) \quad (2)$$

Where A and B are given as the following equations (3) and (4):

$$A = M1g \cdot L1 + M2g \cdot L2 + \ldots - m1g \cdot L6 - \ldots \quad (3)$$

$$B = M2g \cdot (L3+\alpha) + \ldots - m1g \cdot L7 - \ldots \quad (4)$$

When A and B are equal to zero, so that simultaneous equations, each of which corresponds to a corresponding one of the equations (3) and (4) whose left-hand side is set to zero, are obtained. Thus, solving the simultaneous equations for M1 and M2 obtains the values of the weights M1 and M2 to counterbalance the value of the weight m1. Because the value of the weight m1 is determined in consideration of the supporting force for supporting the forearm A upward, it is possible to maintain the supporting force at a desired value, which is, for example, set to be within the range from 500 to 700 g independently of the position of the arm holder 11.

As described above, the arm support apparatus 1 according to the embodiment is configured to allow a doctor D or an assistant to adjust the values M1 and M2 of the counterweights 51 and 53. This adjustment permits the supporting force applied to the forearm 11 upward from the arm holder 11 to be maintained at a desired value independently of the position of the arm holder 11.

Note that, in the embodiment, it is assumed that the influence of the counterweight structure 55 and the rigid link 49, and the influence of swing of the arm holder 11 about the horizontal axis of the joint 37 can be out of consideration. However, the present disclosure is not limited to the assumption. Specifically, an equation for torque $\tau 3$ around the horizontal axis of the joint 37 is written in the same manner as the equations for the torque $\tau 1$ and torque $\tau 2$ assuming that (1) A rotational angle of the rigid link 45 around the horizontal axis of the joint 37 with respect to the rigid link 43 is set to $\theta 3$ (2) A weight of the counterweight structure 55 is referred to as M3.

Thus, solving the simultaneous equations with three unknowns M1, M2, and M3 obtains the values of the weights M1, M2, and M3 to counterbalance with the value of the weight m1. This makes it possible to further reliably maintain the supporting force at a desired value, which is, for example, set to be within the range from 500 to 700 g independently of the position of the arm holder 11.

Specifically, the multijoint arm 12 of the arm support apparatus 1 is designed to have five degrees of freedom corresponding to the joints 31, 32, 33, 37, and 38. Particularly, the multijoint arm 12 is designed to have specified three degrees of freedom around the horizontal axes, perpendicular to the vertical axis, of the respective joints 32, 33, and 37. Thus, the arm support apparatus 1 is comprised of the counterweight structures 51, 53, and 55 attached to the respective rigid links 41, 44, and 49 that are associated with the specified three degrees of freedom; the counterweight structures 51, 53, 55 are designed such that their weights are adjustable. Thus, the arm support apparatus 1 makes it possible to establish the simultaneous equations for three unknown weights M1, M2, and M3 of the respective counterweight structures 51, 53, and 55, and solve the simultaneous equations. This obtains proper weights M1, M2, and M3 for the respective counterweight structures 51, 53, and 55 required to maintain the supporting force applied to the forearm A upward from the arm holder 11 at a desired value. Thus, adjusting the respective counterweight structures 51, 53, and 55 to the obtained the proper weights M1, M2, and M3 makes it possible to reliably maintain the supporting force applied to the forearm A upward from the arm holder 11 at a desired value.

Even if the counterweight structures 51, 53, and 55 take only discrete values, adjustment of the center axis of at least one of the counterweight structures 53 and 55 causes the supporting force to approach a desired constant value. Thus, a doctor D can smoothly perform fine surgical operations, such as sutures of 1 mm or smaller vessels. In other words, the arm support apparatus 1 is configured such that the supporting force is adjustable for various conditions including 1. The type of a surgical operation to be carried out, such as brain surgery, otological surgery, or the like 2. The age and/or experience of a doctor D carrying out a surgical operation 3. Whether a doctor D wants to perform a surgical operation while being sitting on the chair C.

The arm support apparatus 1 is configured such that the brakes 32A, 33A, and 37A are attached to the respective joints 32, 33, and 37 for locking rotation of the respective joints 32, 33, and 37. The arm support apparatus 1 is also configured to set the operation mode of the arm support apparatus 1 to the lock mode according to a doctor's or assistant's input instruction to the controller 13. This activates the brakes 32A, 33A, and 37A, thus fixing the arm holder 11 to a desired position.

Specifically, as described above, the arm support apparatus 1 is configured such that no elastic members, such as springs, and no actuators, such as motors, are used for the multijoint arm 12. This configuration more stably maintains the supporting force applied to the forearm A upward from the arm holder 11 at a desired value. At that time, if the operating mode of the arm support apparatus 1 is not set to the lock mode, removal of the forearm A from the arm holder 11 may cause the arm holder 11 to rise due to the action of gravity on the respective counterweight structures 51, 53, and 55. Thus, the arm support apparatus 1 is capable of setting its operating mode to the lock mode to reliably fix the arm holder 11 to a desired position. This prevents the arm holder 11 from unintentionally rising even if a doctor D removes the forearm A of the dominant arm from the arm holder 11.

The arm support apparatus 1 includes the parallel link mechanism 47, i.e., a so-called four-joint link, designed such that 1. The joints 33, 34, 35, and 36 constitute four corners of a parallelogram shape 2. The opposite sides, i.e. links 41 and 42, of a first pair are equal in length and parallel to each other, and the opposite sides, i.e. links 40 and 44a, of a second pair are equal in length and parallel to each other.

The arm support apparatus 1 also includes the counterweight structure 51 attached to the rigid link 41 swingably coupled to the joint 32, and the counterweight structure 53 attached to the rigid link 44 joined to the rigid link 41 via the joint 35; the height of the joint 32 is maintained at a predetermined constant value. This configuration makes it possible to simplify calculation of a proper weight of each of the counterweight structures 51 and 53.

The present disclosure is not limited to the aforementioned embodiment, and various modifications of the embodiment can be performed within the scope of the present disclosure.

The counterweight structures can be attached to other positions of the multijoint arm 12 different from the aforementioned positions according to the embodiment. The arm support apparatus 1 can be applied to devices each including a more complicated link structure that is equipped with many joints and many rigid links, such as a desk lamp device. In this modification, the arm support apparatus 1 can be comprised of counterweight structures attached to respective rigid links that are associated with specified degrees of freedom. At least one of the specified degrees of freedom can correspond to an oblique axis extending obliquely with respect to the vertical axis of the arm support apparatus 1 while crossing the vertical axis of the arm support apparatus 1.

Various types of mechanisms for adjusting the minimum distance of the center axis of at least one counterweight structure to a corresponding joint can be used.

Figure 6:
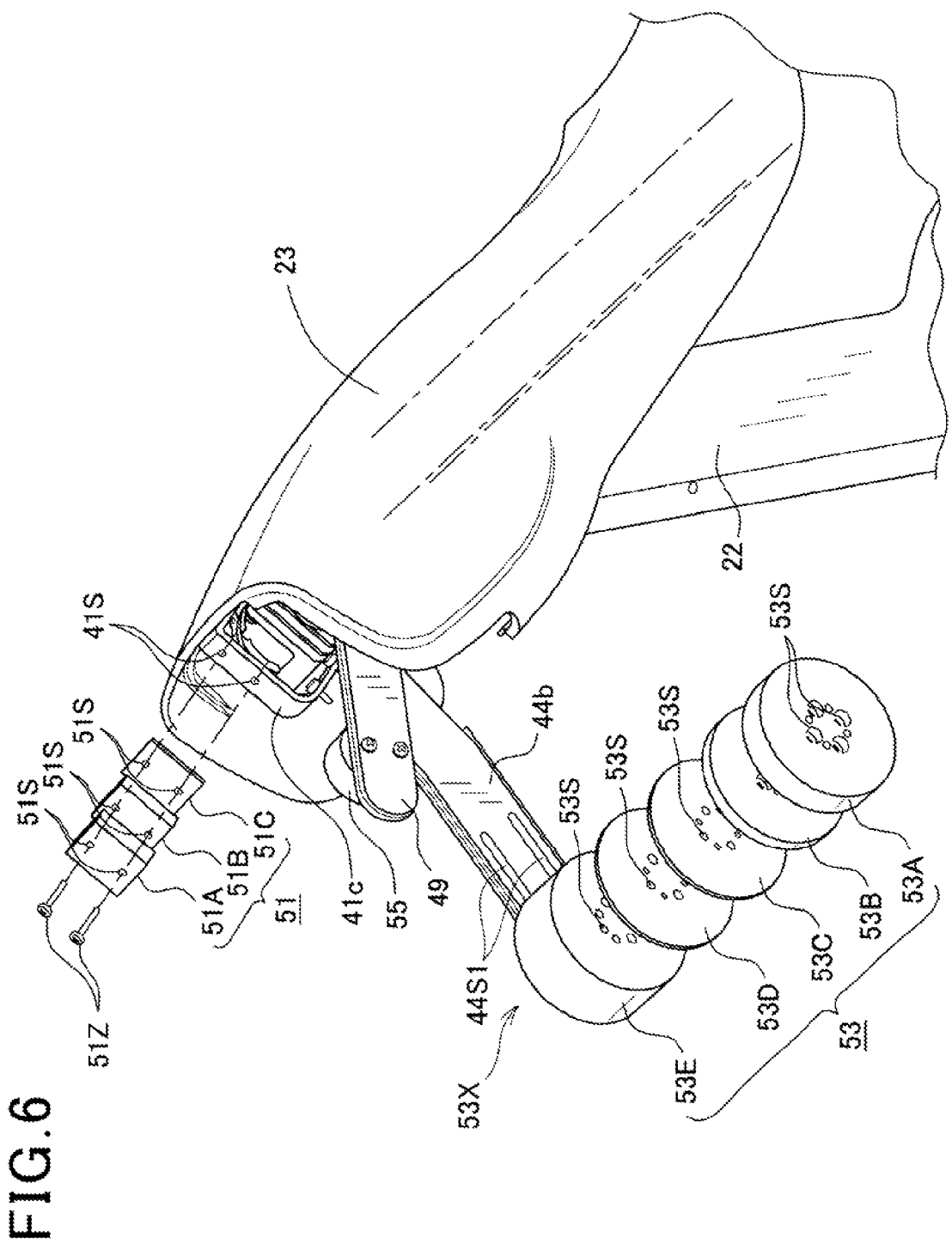
FIG. 6 is an enlarged view schematically illustrating a part of another counterweight structure according to a first modification of the arm support apparatus according to the embodiment.

FIG. 6 schematically illustrates a counterweight structure 53X according to a first modification of the embodiment. As illustrated in FIG. 6, the extending end of the second link member 44b of the rigid link 44 is formed with a pair of long through holes 44S 1 for fixing at least one of the weight members 53A to 53E to the extending end of the second link member 44b. Each of the long through holes 44S1 extends in the length direction of the second link member 44b. A desired number of weight member(s) in the weight members 53A to 53E are mounted on a desired position of the pair of long through holes 44S1. Then, bolts are inserted through the through holes 53S of the desired number of weight member(s) and through the long through holes 44S1, and thereafter, the bolts can be fastened by nuts. As a result, the desired number of weight member(s) in the weight members 53A to 53E are fixedly attached to the extending end of the second link member 44b while the minimum distance of the center axis of the counterweight structure 53 relative to the joint 36 is adjusted.

For the counterweight structure 51 according to a second modification, as illustrated in FIG. 3, one end portions of the screws 51Z can be fixedly fitted in a desired number of weight member(s) in the weight members 51A to 51C while the other end portions can extend from the desired number of weight member(s). Then, the other end portions of the screws 51Z can be inserted into the respective threaded holes 41S while the inserted lengths of the other end portions of the screws 51Z into the respective threaded holes 41S can be adjusted. This makes it possible to adjust the minimum distance of the center axis of the counterweight structure 51 relative to the joint 35.

Figure 7:
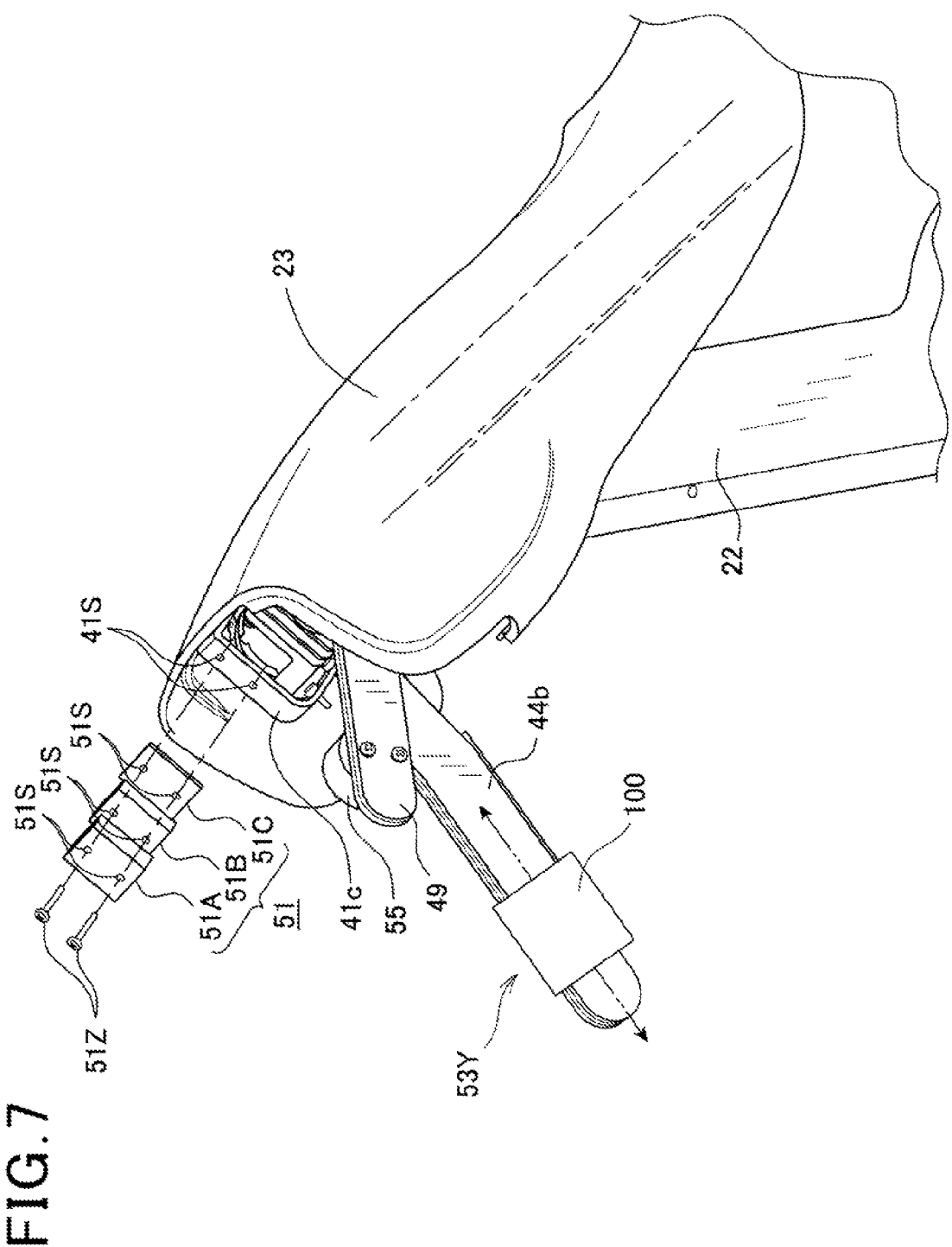
FIG. 7 is an enlarged view schematically illustrating a part of a further counterweight structure according to a third modification of the arm support apparatus according to the embodiment.

FIG. 7 schematically illustrates a counterweight structure 53Y according to a third modification of the present disclosure. As illustrated in FIG. 7, the counterweight structure 53Y includes a mount member 100; the mount member 100 is mounted on the extending end of the second link member 44b of the rigid link 44 so as to be movable along the length direction of the rigid link 44. The mount member 100 is fixable at a desired position in the length direction of the second link member 44b of the rigid link 44. On the mount member 100, a desired number of weight member(s) in the weight members 53A to 53E are fixedly mounted. This configuration of the counterweight structure 53Y according to the third modification makes it possible to adjust the minimum distance of the center axis of the counterweight structure 53 relative to the joint 36.

At least some of the brakes 31A, 32A, 33A, and 37A can be eliminated from the arm support apparatus 1.

The arm support apparatus 1 according to the embodiment is applied for supporting one arm of a doctor who is performing surgical operations, but the present disclosure is not limited to this application. Specifically, the arm support apparatus according to the embodiment can be applied for supporting one arm of an operator who performs operations to, for example, manufacture various machines or devices, such as precise machines of devices.

While the illustrative embodiment of the present disclosure has been described herein, the present disclosure is not limited to the embodiment described herein, but includes any and all embodiments having modifications, omissions, combinations (e.g., of aspects across various embodiments), adaptations and/or alternations as would be appreciated by those in the art based on the present disclosure. The limitations in the claims are to be interpreted broadly based on the language employed in the claims and not limited to examples described in the present specification or during the prosecution of the application, which examples are to be construed as non-exclusive.

What is claimed is:

1. An arm support apparatus to be installed on a reference plane for supporting an arm of an operator, the arm support apparatus comprising:
   a mount on which a part of the arm of the operator is mountable;
   a support member including a plurality of links and a plurality of joints each rotatably supporting at least one of the plurality of links, the support member supporting the mount to be movable based on rotation of at least one of the plurality of links around a corresponding at least one of the plurality of joints, the plurality of joints providing several degrees of freedom, the several degrees of freedom including at least one specified degree of freedom around an axis of at least one joint in the plurality of joints, the axis of the at least one joint being directed to cross a vertical direction of the reference plane; and
   a weight attachment provided for at least one specified link in the plurality of links, the at least one specified link being associated with the at least one specified degree of freedom, the weight attachment being configured such that one or more weight members are attachable thereto, when the one or more weight members are attached to the weight attachment, the weight attachment being configured to substantially balance in weight with the mount on which the part of the arm is mounted while applying supporting force to the part of the arm mounted on the mount, wherein:
   the one or more weight members are a plurality of weight members, and the plurality of weight members have a reference line passing through predetermined points thereof;
   the weight attachment is configured such that a minimum distance between the reference line and the at least one specified link is adjustable; and
   the plurality of weight members are removably attached to the weight attachment, so that the plurality of weight members can be increased or decreased in number.

2. The arm support apparatus according to claim 1, further comprising:
   at least one brake attached to the at least one joint and configured to limit rotation of the at least one specified link around the axis of the at least one joint.

3. The arm support apparatus according to claim 1, wherein:
   the several degrees of freedom include, as the at least one degree of freedom, first and second specified degrees of freedom each around an axis of a corresponding one of a first joint and a second joint as the at least one joint in the plurality of joints, the axis of each of the first and second joints being directed to cross the vertical direction; and
   the weight attachment includes first and second weight attachments each provided for a corresponding one of first and second specified links as the at least one specified link in the plurality of links, the first and second specified links being associated with the respective first and second specified degrees of freedom, each of the first and second weight attachments being configured such that the one or more weight members are attachable thereto.

4. The arm support apparatus according to claim 1, wherein:
   the plurality of joints includes first, second, third, and fourth joints,
   the plurality of links includes first, second, third, and fourth rigid links,
   the first, second, third, and fourth joints constitute four corners of a parallelogram shape,
   the first and second links constitute a first pair of opposite sides of the parallelogram shape,
   the third and fourth links constitute a second pair of opposite sides of the parallelogram shape,
   the at least one joint is at least one specified joint different from the first to fourth joints, and has a constant height relative to the reference plane even if the mount is moved by the support member,
   the first link is joined to the at least one specified joint, and
   the at least one specified link includes the first link, and one of the second to fourth links rotatably coupled to the first link via one of the first to fourth joints.

\* \* \* \* \*